(12) United States Patent
Collin et al.

(10) Patent No.: US 8,241,616 B2
(45) Date of Patent: Aug. 14, 2012

(54) HAIR STYLING COMPOSITION

(75) Inventors: Jennifer Reichl Collin, Devon, PA (US); Michael Paul Hallden-Abberton, Maple Glen, PA (US); Beth Ann Falcone, Feasterville, PA (US); Miao Wang, Schwenksville, PA (US); Fanwen Zeng, Belle Mead, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 506 days.

(21) Appl. No.: 12/384,030

(22) Filed: Mar. 31, 2009

(65) Prior Publication Data

US 2009/0252689 A1    Oct. 8, 2009

Related U.S. Application Data

(60) Provisional application No. 61/072,899, filed on Apr. 3, 2008.

(51) Int. Cl.
| | |
|---|---|
| *A61K 8/00* | (2006.01) |
| *A61K 8/18* | (2006.01) |
| *A61Q 5/00* | (2006.01) |
| *A61Q 9/00* | (2006.01) |
| *A61Q 7/00* | (2006.01) |
| *A61Q 5/06* | (2006.01) |
| *A61K 5/12* | (2006.01) |
| *A61K 8/73* | (2006.01) |
| *A61K 8/81* | (2006.01) |
| *A61K 9/12* | (2006.01) |
| *A01K 8/02* | (2006.01) |
| *A01N 25/02* | (2006.01) |
| *C07D 3/37* | (2006.01) |

(52) U.S. Cl. ............... 424/70.1; 424/70.11; 424/70.12; 424/70.13; 424/70.15; 424/70.16; 424/43; 424/47; 424/359; 424/361; 424/362; 424/401; 510/406; 510/475

(58) Field of Classification Search ............... 424/70.1, 424/70.11, 70.12, 70.13, 70.15, 70.16, 43, 424/47, 359, 361, 362, 401; 162/164.1; 510/406, 510/475
See application file for complete search history.

(56) References Cited

U.S. PATENT DOCUMENTS

| | | | |
|---|---|---|---|
| 4,261,972 A | | 4/1981 | Nandagiri |
| 4,315,910 A | | 2/1982 | Nowak |
| 5,686,067 A | * | 11/1997 | Shih et al. .................. 424/70.15 |
| 5,948,396 A | | 9/1999 | Das et al. |
| 6,136,884 A | * | 10/2000 | Chen et al. .................. 523/105 |
| 2004/0096474 A1 | | 5/2004 | Merlau |
| 2008/0216978 A1 | * | 9/2008 | Baxter et al. ............... 162/164.1 |

FOREIGN PATENT DOCUMENTS

| | | |
|---|---|---|
| CA | 2168947 A1 | 2/1995 |
| EP | 0364887 | 4/1990 |
| EP | 1371705 A1 | 12/2003 |
| EP | 1488774 A2 | 12/2004 |
| EP | 1530962 A1 | 5/2005 |
| JP | 55038310 | 3/1980 |
| JP | 2002308722 | 10/2002 |
| JP | 2006233013 | 9/2006 |
| WO | WO 2007/075969 | 7/2007 |

* cited by examiner

*Primary Examiner* — Johann Richter
*Assistant Examiner* — Jane C Oswecki
(74) *Attorney, Agent, or Firm* — Carl P. Hemenway

(57) ABSTRACT

There is provided a hair styling composition comprising
  (a) one or more fully soluble polymer,
  (b) solvent-propellant mixture or solvent mixture, and
    optional other ingredients.
Also provided is a method of making polymer.

14 Claims, No Drawings

HAIR STYLING COMPOSITION

This application claims the benefit of priority under 35 U.S.C. §119(e) of U.S. Provisional Patent Application No. 61/072,899 filed on Apr. 3, 2008.

BACKGROUND

Hair styling formulations are desired that provide both good hold (i.e., the ability to hold hair in place) and good shine (i.e., the ability to give hair a shiny appearance). In the past, hair styling formulations contained certain polymers that caused the formulations to have good hold, but these formulations lacked the level of shine that is desired by consumers. In the past, some of such formulations also had one or more additive such as, for example, organic-substituted silicone. The additive was sometimes effective at increasing shine, but it also reduced the ability of the formulation to hold hair.

Because hair styling compositions are sometimes sprayed, it is also desirable that any polymers used in the composition dissolve fully in an appropriate solvent. Further, for proper spraying, it is desirable that a solution of any polymers used in the composition should have viscosity that is not too high. Also, it is desirable that the hair styling composition be stable (i.e., that none of the ingredients settles while the composition is in storage). Additionally, it is desirable that a hair styling composition, after it is dry, be easy to remove, for example by washing with shampoo.

U.S. Pat. No. 4,315,910 describes aerosol hair spray compositions that contain polymer, including, for example styrene/maleic anhydride polymers. It is desired to provide hair styling formulations that provide both good hold and good shine. It is also desired to provide polymers suitable for such formulations, where such polymers are fully soluble and where such polymers form solutions that have viscosity that is not too high. It is also desired to provide polymers that can be used in hair styling compositions that are removable when dry.

STATEMENT OF THE INVENTION

In a first aspect of the present invention, there is provided a hair styling composition comprising
(a) one or more fully soluble polymer comprising, as polymerized units,
  (i) 30% to 75% by weight, based on the weight of said polymer, one or more monomer that has refractive index of 1.490 or higher,
  (ii) 1% to 30% by weight, based on the weight of said polymer, one or more acid-functional monomer, and
  (iii) 5% to 69% by weight, based on the weight of said polymer, one or more additional monomer,
(b) solvent-propellant mixture comprising
  (i) 0% to 75% by weight, based on the weight of said solvent-propellant mixture, propellant,
  (ii) 5% to 95% by weight, based on the weight of said solvent-propellant mixture, volatile organic solvent, and
  (iii) 0% to 50% by weight, based on the weight of said solvent-propellant mixture, water,
(c) neutralizer, wherein the mole ratio of said neutralizer to the acid-functional groups on said polymer (a) is from 0:1 to 1.1:1, and
(d) one or more adjuvants, wherein the ratio of the total weight of all adjuvants to the weight of said polymer (a) is from 0:1 to 1.4:1,
wherein the amount of said polymer (a) is 1% to 10% by weight based on the sum of the weights of said polymer (a) and said solvent-propellant mixture (b), wherein the amount of said solvent-propellant mixture (b) is 90% to 99% by weight based on the sum of the weights of said polymer (a) and said solvent-propellant mixture (b).

In a second aspect of the present invention, there is provided a hair styling composition comprising
  (AA) one or more fully soluble polymer with the same definition as polymer (a) defined above,
  (BB) solvent mixture comprising
    (i) 0% to 50% by weight, based on the weight of said solvent mixture, volatile organic solvent, and
    (ii) 50% to 100% by weight, based on the weight of said solvent mixture, water,
  (c) neutralizer, as described herein above,
  (d) one or more adjuvants, as described herein above
wherein the amount of said polymer (AA) is 1% to 20% by weight based on the sum of the weights of said polymer (AA) and said solvent mixture (BB), wherein the amount of said solvent mixture (BB) is 80% to 99% by weight based on the sum of the weights of said polymer (AA) and said solvent mixture (BB).

In a third aspect of the present invention, there is provided a method for making a polymer comprising emulsion polymerization of one or more monomer mixture, wherein said monomer mixture comprises monomers (i), (ii), and (iii) as defined herein above, wherein said emulsion polymerization is conducted partially or entirely in the presence of one or more nonionic surfactant and one or more chain transfer agent.

DETAILED DESCRIPTION

A "hair styling composition" as used herein is a composition that may be used on hair to hold the hair in a particular shape or configuration. Such compositions typically contain various polymeric resins, gums, and/or adhesive agents designed to impart desirable properties to the compositions and, ultimately, to hair upon which the compositions are applied. The polymers are used for a variety of purposes including, for example, one or more of hair holding, improving volume, improving appearance, and imparting desirable feel properties. Much of the ability of hair styling compositions to hold the hair in a particular shape results from one or more polymer used in the compositions. Hair styling compositions include, for example, hair sprays, styling gels, spray gels and mousses.

A "polymer," as used herein and as defined by F W Billmeyer, JR. in *Textbook of Polymer Science*, second edition, 1971, is a relatively large molecule made up of the reaction products of smaller chemical repeat units.

Polymer molecular weights can be measured by standard methods such as, for example, size exclusion chromatography (SEC, also called gel permeation chromatography or GPC). Generally, polymers have weight-average molecular weight (Mw) of 1,000 or more. Some polymers are characterized by Mn, the number-average molecular weight.

As used herein "weight of polymer" means the dry weight of polymer. Molecules that can react with each other to form the repeat units of a polymer are known herein as "monomers." One example of a class of monomers that are useful in the present invention are, for example, ethylenically unsaturated monomers (i.e., monomers that have at least one carbon-carbon double bond). Typical ethylenically unsaturated monomers have molecular weight of less than 500. Among such monomers are, for example, vinyl monomers. Some suitable vinyl monomers include, for example, styrene, substituted styrenes, dienes, ethylene, ethylene derivatives, and mixtures thereof. Ethylene derivatives include, for example, unsubstituted or substituted versions of the following: vinyl acetate, acrylonitrile, (meth)acrylic acids, (meth)acrylates, (meth)acrylamides, vinyl chloride, halogenated alkenes, and mixtures thereof. As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof.

A polymer that is made by polymerizing a certain monomer, either alone or with other monomers, is said herein to include that monomer as a polymerized unit.

As used herein, "normal boiling point" of a compound is the boiling point at one atmosphere pressure. As used herein, a "volatile" compound is a compound with normal boiling point of 250° C. or lower. As used herein, "INCI" is the International Nomenclature of Cosmetic Ingredients.

As used herein, an "organic" compound is any compound that contains one or more carbon atoms except for those carbon-containing compounds that are generally accepted to be inorganic compounds. Examples of carbon-containing compounds that are generally accepted to be inorganic compounds include the following: carbon oxides (such as, for example, carbon dioxide), carbon disulfide, metallic cyanides, metallic carbonyls, phosgene, carbonyl sulfide, metallic carbonates, and metallic bicarbonates.

In some embodiments, hair styling composition of the present invention is suitable as a hair spray. In some of such embodiments, hair styling composition is suitable as a pump spray or as an aerosol spray. In some of such embodiments, hair styling composition is suitable as an aerosol spray.

Hair styling composition of the present invention contains one or more polymer (known herein as "polymer (a)"). As used herein, "polymer (AA)" has the same characteristics as "polymer (a)." In some embodiments, polymer (a) contains one or more vinyl polymer. In some embodiments, every polymer (a) in the hair styling composition is a vinyl polymer. As used herein, a vinyl polymer is a polymer made by polymerization of vinyl monomers. In some embodiments, a vinyl polymer is made by free radical polymerization of vinyl monomers.

Independent of the composition of polymer (a), in some embodiments, one or more polymer (a) is used that has Mw of 25,000 or higher, or 50,000 or higher. Independently, in some embodiments, one or more polymer (a) is used that has Mw of 300,000 or lower, or 150,000 or lower. Independently, in some embodiments, every polymer (a) has Mw of 25,000 to 300,000.

Polymer (a) of the present invention contains polymerized units of one or more monomer (known herein as "monomer (i)") that has refractive index of 1.490 or higher. Refractive index of a monomer can be measured, for example, by ASTM Standard D1218-02, at 25° C. In some embodiments, monomer (i) contains one or more monomer with refractive index of 1.500 or higher; or 1.530 or higher. In some embodiments, every monomer (i) is a monomer with refractive index of 1.530 or higher.

In some embodiments, monomer (i) contains one or more vinyl monomer. In some embodiments, monomer (i) contains one or more vinyl aromatic monomer. A vinyl aromatic monomer is a monomer that contains one or more carbon-carbon double bond and one or more aromatic ring. Suitable vinyl aromatic monomers include, for example, monomers with benzyl groups, monomers with phenyl groups, styrene, derivatives of styrene (such as, for example, alpha-methyl styrene), and mixtures thereof. In some embodiments, every monomer (i) is a vinyl aromatic monomer. In some embodiments, monomer (i) comprises one or more of styrene, alpha-methyl styrene, or a mixture thereof. In some embodiments, every monomer (i) is selected from styrene, alpha-methyl styrene, and mixtures thereof.

Mixtures of suitable monomers (i) are also suitable.

The amount of polymerized units of monomer (i) in the polymer (a) of the present invention is 30% to 75% by weight, based on the weight of the polymer (a). In some embodiments, the amount of polymerized units of monomer (i) is 35% or more, or 39% or more, by weight, based on the weight of the polymer. In some embodiments, the amount of polymerized units of monomer (i) is 65% or less, or 55% or less, by weight, based on the weight of the polymer.

Polymer (a) of the present invention additionally contains one or more polymerized unit of one or more monomer (herein called "monomer (ii)") that has at least one acid-functional group. Suitable acid-functional groups include, for example, sulfonic acid groups and carboxylic acid groups. The acid-functional groups may be in neutral form or ionic form or a mixture thereof. Some suitable monomer (ii) include, for example, vinyl monomers with at least one acid-functional group. Independently, in some embodiments at least one monomer (ii) with a carboxylic acid group is used. In some embodiments, every monomer (ii) has a carboxylic acid group.

Suitable monomers (ii) having sulfonic acid group include, for example, 2-acrylamido-2-methylpropane sulfonic acid. Suitable monomers (ii) include, for example, acrylic acid, methacrylic acid, and mixtures thereof.

In some embodiments, monomer (ii) comprises at least one monomer that has exactly one acid-functional group.

In some embodiments, polymer (a) of the present invention does not include any polymerized unit of maleic anhydride. In some embodiments, polymer (a) of the present invention does not include any polymerized unit of any monomer with any anhydride group. In some embodiments, polymer (a) of the present invention does not include any polymerized unit of any monomer with more than one carboxyl group. In some embodiments, polymer (a) of the present invention does not include any polymerized unit of any monomer with more than one acid-functional group.

Mixtures of suitable monomers (ii) are also suitable.

The amount of polymerized units of monomer (ii) in the polymer is 1% to 30% by weight, based on the weight of the polymer. In some embodiments, the amount of polymerized units of monomer (ii) in the polymer is 2% or more; or 5% or more; or 10% or more; or 12% or more, or 14% or more, or 18% or more, or 20% or more, or 22% or more, by weight, based on the weight of the polymer.

In some embodiments, every monomer (i) that is present is a monomer that has no acid functional group. Independently, in some embodiments, every monomer (ii) that is present is a monomer that has index of refraction below 1.490. Also contemplated are embodiments in which every monomer (i) that is present is a monomer that has no acid functional group and in which every monomer (ii) that is present is a monomer that has index of refraction below 1.490.

Also contemplated are embodiments in which one or more monomer is used that has index of refraction of 1.490 or greater and also has at least one acid functional group. In such embodiments, it is contemplated to calculate the amount of polymerized units of monomers (i) and (ii) in polymer (a) by finding the total weight of polymerized units of monomers that have index of refraction of 1.490 or greater or that have at least one acid functional group or that have both index of refraction of 1.490 and at least one functional group, counting each polymerized unit once. That total weight will be 31% to 95% by weight, based on the weight of polymer (a).

Among embodiments in which one or more monomer is used that has index of refraction of 1.490 or greater and also has at least one acid functional group, some suitable such monomers are, for example, styrenesulfonic acid and substituted styrene sulfonic acids.

The polymer (a) of the present invention additionally contains polymerized units of one or more additional monomer (known herein as "monomer (iii)"). Monomer suitable as monomer (iii) is monomer that is not monomer (i) and is not monomer (ii). In some embodiments, monomer (iii) includes one or more vinyl monomer. In some embodiments, every monomer (iii) is a vinyl monomer.

Some suitable monomers (iii) include, for example, olefins, dienes, and (meth)acrylate monomers. As used herein, (meth)acrylate monomers include substituted and unsubstituted esters and amides of acrylic acid and methacrylic acid. Some suitable monomers (iii) include, for example, alkyl esters of (meth)acrylic acid, including, for example, those in which the alkyl group is linear, branched, cyclic, or a combination thereof, with 1 to 20 carbon atoms. In some embodiments, monomer (iii) includes one or more $C_1$-$C_{20}$ alkyl acrylate. In some embodiments, monomer (iii) includes one or more alkyl acrylate with 2 or more carbon atoms, or with 3 or more carbon atoms. Independently, in some embodiments, monomer (iii) includes one or more alkyl acrylate with 10 or fewer carbon atoms, or with 8 or fewer carbon atoms. In some embodiments in which one or more alkyl acrylate is used, the amount of polymerized units of alkyl acrylate monomer in the polymer is 5% or more, or 10% or more, by weight based on the weight of the polymer. Independently, in some embodiments in which one or more alkyl acrylate is used, the amount of polymerized units of alkyl acrylate monomer in the polymer is 50% or less, or 40% or less, by weight based on the weight of the polymer.

Independently, in some embodiments, monomer (iii) includes one or more $C_1$-$C_{20}$ alkyl methacrylate. In some embodiments, monomer (iii) includes one or more alkyl methacrylate with 6 or fewer carbon atoms, or with 3 or fewer carbon atoms, or with 2 or fewer carbon atoms. In some embodiments, monomer (iii) contains one or more alkyl acrylate and also contains one or more alkyl methacrylate. In some embodiments in which one or more alkyl methacrylate is used, the amount of polymerized units of alkyl methacrylate monomer in the polymer is 3% or more, or 6% or more, by weight based on the weight of the polymer. Independently, in some embodiments in which one or more alkyl methacrylate is used, the amount of polymerized units of alkyl methacrylate monomer in the polymer is 25% or less, or 12% or less, by weight based on the weight of the polymer.

Independently, some suitable monomers (iii) also include, for further example, substituted-alkyl esters of (meth)acrylic acid, which have the structure of alkyl esters of (meth)acrylic acid in which the ester group has one or more substituent group such as, for example, one or more hydroxyl group. Some suitable monomers (iii) include, for example, hydroxyalkyl esters of (meth)acrylic acid in which the alkyl group has 1 to 10 carbon atoms. In some embodiments, monomer (iii) contains one or more hydroxyalkyl ester of (meth)acrylic acid in which the alkyl group has 6 or fewer carbon atoms, or 4 or fewer carbon atoms. Some suitable hydroxyalkyl esters of (meth)acrylic acid include, for example, hydroxypropyl (meth)acrylate, hydroxyethyl (meth)acrylate, and mixtures thereof. In some embodiments in which one or more substituted-alkyl ester of (meth)acrylic acid is used, the amount of polymerized units of substituted-alkyl ester of (meth)acrylic acid in the polymer is 2% or more, or 5% or more, by weight based on the weight of the polymer. Independently, in some embodiments in which one or more substituted-alkyl ester of (meth)acrylic acid is used, the amount of polymerized units of substituted-alkyl ester of (meth)acrylic acid in the polymer is 40% or less, or 20% or less, by weight based on the weight of the polymer.

In some embodiments, monomer (iii) contains one or more alkyl acrylate, one or more alkyl methacrylate, and one or more substituted-alkyl (meth)acrylate.

In some embodiments, monomer (iii) does not contain any substituted-alkyl (meth)acrylate.

In some embodiments, the sum of the amount polymerized units of monomer (ii) plus the amount polymerized units of hydroxyalkyl esters of (meth)acrylic acid is, by weight based on the weight of the polymer, 10% or more, or 20% or more. Independently, in some embodiments, the sum of the amount of polymerized units of monomer (ii) plus the amount of polymerized units of hydroxyalkyl esters of (meth)acrylic acid is, by weight based on the weight of the polymer, 50% or less, or 40% or less.

In some embodiments, the amount of hydroxyalkyl esters of (meth)acrylic acid is 5% or less, or 0%, and the amount of monomer (ii) is 20% or more, by weight based on the weight of the polymer.

Independent of the composition of monomer (iii), the total amount in the polymer (a) of the present invention of polymerized units of all monomer or monomers (iii) is 30% to 89% by weight based on the weight of the polymer (a). In some embodiments, the total amount of polymerized units of monomer (iii) is 75% or less, or 60% or less, by weight based on the weight of the polymer (a).

Mixtures of suitable monomers (iii) are also suitable.

In some embodiments, one or more chain transfer agent is used in the polymerization of polymer (a). Chain transfer agents are compounds that are effective at promoting chain transfer process during free-radical polymerization. It is contemplated that chain transfer agents act to reduce the molecular weight of the polymer that is produced by the polymerization process. Some suitable chain transfer agents include, for example, mercaptans, sulfides, and halides. Some suitable halides, for example, include alkyl halides, such as, for example, halomethanes and halogenated esters (such as, for example, halogenated acetates). Suitable sulfides include, for example, dialkyl disulfides, diaryl disulfides, diaroyl disulfides, and xanthogens. Some suitable mercaptans include, for example, unsubstituted alkyl mercaptans and substituted alkyl mercaptans. Substituted alkyl mercaptans include, for example, compounds in which one or more hydroxyl group and/or one or more carboxyl group is attached to the alkyl portion of the molecule, in addition to the one or more thiol group. In some embodiments, one or more unsubstituted alkyl mercaptan is used.

In some of the embodiments in which one or more chain transfer agent is used, the amount of chain transfer agent, in millimoles per 100 grams of total monomer, is 0.5 or more; or 1 or more; or 2 or more. Independently, in some of the embodiments in which one or more chain transfer agent is used, the amount of chain transfer agent, in millimoles per 100 grams of total monomer, is 20 or less; or 10 or less; or 5 or less.

In some embodiments, polymer (a) of the present invention does not include any polymerized unit of any monomer that is a vinyl lactam. Independently, in some embodiments, polymer (a) of the present invention does not include any polymerized unit of any monomer that is an amide of acrylic acid or an amide of methacrylic acid. Independently, in some embodiments, polymer (a) of the present invention does not include any polymerized unit of any monomer that is an amide compound. Independently, in some embodiments, polymer (a) of the present invention does not include any polymerized unit of vinyl acetate. Independently, in some embodiments, polymer (a) of the present invention does not include any polymerized unit of any monomer that has molecular weight of 500 or greater.

Independently, in some embodiments, all of the polymerized units in the polymer (a) of the present invention are selected from the group consisting of styrene, alkyl-substituted styrene, alkyl esters of (meth)acrylic acid, hydroxyalkyl esters of (meth)acrylic acid, chain transfer agents, and mixtures thereof.

Polymer (a) is a fully soluble polymer. As used herein, "fully soluble" means that the polymer meets the following criterion. A polymer test solution is made and tested for turbidity as described in the Examples section below. A polymer is considered herein to be fully soluble if it has turbidity of 120 NTU or lower in a solution with 12% polymer solids (by weight based on the weight of the solution) or if it has turbidity of 100 NTU or lower in a solution with 10% polymer solids (by weight based on the weight of the solution).

In some embodiments, polymer (a) has "enhanced solubility," which means herein that it has turbidity of 20 NTU or lower in a solution with 10% polymer solids (by weight based on the weight of the solution).

Independent of the degree of solubility of polymer (a), in some embodiments, compositions of the present invention are storage stable. That is, after storage in a closed container for 6 months, there is no visible precipitate and there is no change in the turbidity. In some embodiments, there is no visible precipitate and there is no change in the turbidity after storage for 18 months.

A polymer is considered herein to be fully soluble if and only if it meets the above criterion. It is contemplated that, in general, when a polymer that is fully soluble is observed in circumstances other than the turbidity test described below, it may be part of a system that is optically clear or may be part of a system that is turbid. For illustration, it is useful to consider an example polymer that was made by emulsion polymerization at pH of less than 6 and is observed in the form of the latex that was a produced by the emulsion polymerization; such an example polymer could be observed as having 45% solids and having pH of less than 6. In some cases, such a latex could be turbid, and nevertheless it is still possible that the polymer, when subjected to the turbidity test described below (which involves neutralization to higher pH and dilution with ethanol and water), could yield turbidity low enough that the polymer could qualify as "fully soluble" herein.

In some embodiments, polymer (a) is made by emulsion polymerization and exits in the form of a latex. In some of such embodiments, a portion of the complete latex is added to some appropriate solvent for the purpose, for example, of turbidity testing. In such cases, it is contemplated that latex that is added to the solvent will contain, in addition to the polymer itself, other compounds such as, for example surfactant or surfactants remaining in the latex from the emulsion polymerization process. When such a latex of polymer (a) of the present invention is tested, it will be shown to be fully soluble. That is, the test solution, which contains all of the compounds of the latex, will have sufficiently low turbidity.

It is contemplated that a latex of polymer (a) of the present invention can be fully soluble even if one or more of the compounds present in the latex is not soluble. While the present invention is not limited to any theory, it is considered that, in some embodiments, one or more surfactant (or other compound in the latex) will be sufficiently compatible with the polymer (a) that the combination of polymer (a) and that surfactant will be fully soluble.

It is useful to characterize compositions of the present invention by the Volatile Organic Compounds (VOC) content. The VOC content of a composition is the amount of all volatile organic compounds, expressed as a percentage by weight based on the total weight of the composition. It is contemplated that, if two or more organic compounds that have normal boiling point of 250° C. or lower are used in the composition, they may or may not be mixed together prior to being added to the composition. In some embodiments, compositions of the present invention have VOC content of 30% to 95%.

In some embodiments, herein called "low-VOC" embodiments, the VOC content of the hair styling composition is between 30% and 65%. In some low-VOC embodiments, the VOC content is 45% or higher; or 50% or higher. Independently, in some low-VOC embodiments, the VOC content is 60% or lower.

It is contemplated that some low-VOC embodiments will be useful as aerosol sprays and that some low-VOC embodiments will be useful as pump sprays.

In some embodiments, herein called "high-VOC" embodiments, the VOC content of the hair styling composition is between 70% and 95%. In some high-VOC embodiments, the VOC content is 75% or higher. Independently, in some high-VOC embodiments, the VOC content is 90% or lower; or 85% or lower.

It is contemplated that some high-VOC embodiments will be useful as aerosol sprays and that some high-VOC embodiments will be useful as pump sprays.

Also contemplated are embodiments, herein called "very-low-VOC" embodiments, in which the VOC content is 0% to less than 30%. In some very-low-VOC embodiments, no propellant is used. It is contemplated that some very-low-VOC embodiments, for example, will be useful as spray gels. Some spray gels contain one or more thickener. In some spray gels in which thickener is used, the amount of thickener has weight ratio of thickener to polymer (a) (or to polymer (AA)) of 0.05:1 to 1:1.

Among the very-low-VOC embodiments are contemplated some embodiments, herein called "extremely-low-VOC" embodiments, in which the VOC content is 0% to 1%. Some extremely-low-VOC embodiments will be useful, for example, as non-aerosol mousses, hair styling gels, hair setting lotions, and hair pomades.

Non-aerosol mousse typically contains one or more betaine surfactant, sometimes in an amount having weight ratio of betaine surfactant to polymer (a) (or to polymer (AA)) of 0.05:1 to 1:1. Hair styling gel typically contains one or more thickener (also called rheology modifier), sometimes in an amount having weight ratio of thickener to polymer (a) (or to polymer (AA)) of 0.05:1 to 0.5:1. Hair setting lotion typically contains one or more fatty compound (i.e., a compound containing, possibly among other chemical groups, a hydrocarbon chain of 8 or more carbon atoms), sometimes in an amount having weight ratio of fatty compound to polymer (a) (or to polymer (AA)) of 0.1:1 to 2:1. In some hair setting lotion, the fatty compound is liquid at 20° C. Waxes are fatty compounds that are solid at 20° C. Hair pomades sometimes contain one or more wax, sometimes in an amount having weight ratio of wax to polymer (a) (or to polymer (AA)) of 0.1:1 to 2:1.

In some embodiments, there is a tendency for the composition to form foam. In some situations, such foam is undesirable. For example, the presence of air bubbles may reduce the shininess of treated hair. Among such embodiments, it is contemplated that a silicone defoamer may, optionally, be added to the composition. If a silicone defoamer is used, the weight ratio of silicone defoamer to polymer (a) may be, for example, from 0.01:1 to 0.5:1, or from 0.05:1 to 0.15:1.

In addition to polymer (a), some compositions of the present invention contain component (b). Component (b) contains water, one or more volatile organic solvent, and, optionally, one or more propellant. The volatile organic solvent contained in component (b) is known herein as "solvent (sb)." Solvent (sb) is liquid at 25° C. and is capable of dissolving polymer (a). In some embodiments, one or more solvent (sb) is used that has boiling point of 200° C. or lower, or 150° C. or lower, or 100° C. or lower. Independently, in some embodiments, one or more solvent (sb) is used that has boiling point of 30° C. or higher, or 45° C. or higher, or 60° C. or higher. In some embodiments, every organic solvent that is used in the hair styling composition is a solvent (sb). Independently, in some embodiments, every organic solvent that is used in the hair styling composition has normal boiling point of 100° C. or lower.

Some suitable solvents (sb) include, for example, hydrocarbons, which may be linear, cyclic, branched, or a combination thereof; ketones; ethers; furans; fully or partially halogenated hydrocarbons; alcohols; aromatic compounds; and mixtures thereof. In some embodiments, the solvent (sb) contains one or more alcohol. Suitable alcohols include, for example, C1-C5 hydrocarbons with a single hydroxy group. One suitable alcohol is ethyl alcohol.

In some embodiments, solvent (sb) is cosmetically acceptable. That is, the solvent (sb) is suitable for use in hair spray and/or cosmetics (i.e., uses that involve contact with human hair and/or skin).

Mixtures of suitable organic solvents are also suitable.

In some embodiments, no organic solvent is used in component (sb) other than one or more alcohol.

The amount of solvent (sb) in component (b) is, by weight, based on the weight of component (b), 5% to 95%. In some embodiments, the amount of solvent (sb) in component (b) is, by weight, based on the weight of component (b), 5% to 90%.

The amount of water in component (b) is, by weight based on the weight of component (b), 0% to 50%. In some embodiments, the amount of water in component (b) is, by weight, based on the weight of component (b), 10% to 50%.

In some embodiments, no propellant is used in component (b).

Among embodiments in which a composition of the present invention is intended to be used in an aerosol spray, an appropriate propellant is also used. Propellants are gaseous at 25° C. and one atmosphere pressure. Some suitable propellants have normal boiling point of 24° C. or lower; or 0° C. or lower; or −20° C. or lower. Independently, some suitable propellants have normal boiling point of −196° C. or higher; or −100° C. or higher; or −50° C. or higher.

In some embodiments, one or more organic propellant is used. In some embodiments, every propellant that is used is organic.

Independent of the boiling point at one atmosphere pressure, some propellants, called "liquefied propellants," are liquid at 25° C. inside a pressurized aerosol can. Some of such liquefied propellants are, for example, halocarbons, hydrocarbons, or mixtures thereof. Some propellants, called "compressed gas propellants," remain gaseous at 25° C. inside a pressurized aerosol can.

Some suitable propellants are, for example, alkanes having 4 or fewer carbon atoms, fluorinated hydrocarbons having 2 carbon atoms, dimethyl ether, and mixtures thereof. Some suitable propellants are, for example, n-butane, isobutane, propane, dimethyl ether, 1,1-difluoroethane, tetrafluoroethane, and mixtures thereof. In some embodiments, the propellant contains one or more of dimethyl ether, 1,1-difluoroethane, tetrafluoroethane, or any mixture thereof. In some embodiments, every propellant is selected from dimethyl ether, 1,1-difluoroethane, tetrafluoroethane, and mixtures thereof.

In some embodiments, a water-soluble propellant is used (i.e., a propellant that is soluble in water at 25° C. at autogenous pressure). The autogenous pressure is the pressure inside a sealed aerosol can that arises from the volatility of the ingredients. One suitable water-soluble propellant is, for example, dimethyl ether. In some embodiments, every propellant that is used is water-soluble. In some embodiments, the only propellant that is used is dimethyl ether.

Among some embodiments in which one or more propellant is used, the amount of propellant, by weight based on the weight of component (b), is 25% or more; or 35% or more; or 45% or more. Independently, among some embodiments in which one or more propellant is used, the amount of propellant, by weight based on the weight of component (b), is 60% or less; or 55% or less.

Among all the various embodiments of the present invention, a few illustrative but not limiting embodiments are contemplated as follows.

In one embodiment, component (b) contains 30% to 50% water, and 50% to 70% solvent (sb), by weight based on the weight of component (b), and no propellant.

In a second embodiment, component (b) contains 5 to 25% water, and 75% to 90% solvent (sb), by weight based on the weight of component (b), and no propellant.

In a third embodiment, component (b) contains 45% to 55% propellant, 30 to 45% water, and 0% to 25% solvent (sb), by weight based on the weight of component (b).

In a fourth embodiment, component (b) contains 40% to 60% propellant, 5% to 25% water, and 15% to 85% solvent (sb), by weight based on the weight of component (b).

In a fifth embodiment, component (b) contains 40% to 60% propellant, 0% to 1% water, and 40% to 60% solvent (sb), by weight based on the weight of component (b).

In a sixth embodiment, component (b) contains 0% to 1% water, 99% to 100% solvent (sb), by weight based on the weight of component (b), and no propellant.

Among embodiments employing component (b), the amount of polymer (a) present in the hair styling composition of the present invention is 1% to 10% by weight based on the sum of the weights of polymer (a) and component (b). In some embodiments, the amount of polymer (a) is 2% or more, or 3% or more, or 4% or more, by weight based on the sum of the weights of polymer (a) and component (b). In some embodiments, the amount of polymer (a) is 8% or less, or 6% or less, or 5% or less, by weight based on the sum of the weights of polymer (a) and component (b).

In addition to polymer (a), some compositions of the present invention contain component (BB). Component (BB) contains water and one or more volatile organic solvent. The volatile organic solvent contained in component (BB) is known herein as "solvent (SBB)." Solvent (SBB) has the same characteristics as solvent (sb) described herein above.

The amount of solvent (SBB) in component (BB) is, by weight, based on the weight of component (BB), 0% to 50%.

The amount of water in component (BB) is, by weight, based on the weight of component (BB), 50% to 100%.

In some embodiments, no propellant is used in component (BB).

Among embodiments employing component (BB), the amount of polymer (a) present in the hair styling composition of the present invention is 1% to 20% by weight based on the sum of the weights of polymer (a) and component (BB). In some embodiments, the amount of polymer (a) is 2% or more, or 3% or more, or 4% or more, by weight based on the sum of the weights of polymer (a) and component (BB). In some embodiments, the amount of polymer (a) is 15% or less, or 12% or less, by weight based on the sum of the weights of polymer (a) and component (b).

In some embodiments, the composition of the present invention contains one or more neutralizing compound. It is contemplated that polymer (a) is soluble in the hair styling composition "as is" or upon neutralization of some or all of the acid-functional groups contained in the polymer (a). The acid-functional groups may be neutralized by conventional techniques with at least one neutralizing compound, which may aid in dissolving the polymer (a) in the hair styling composition. Neutralizing compound, when used, may be selected, for example, from one or more amines, alkali or alkaline earth metal hydroxides, ammonium hydroxide, and mixtures thereof. Suitable amine neutralizers include, for example, 2 amino-2-methyl-1,3-propanediol, 2-amino-2-methyl-1-propanol, N,N-dimethyl-2-amino-2-methyl-1-propanol, mono-isopropanolamine, triisopropanolamine, ethanolamine, triethanolamine, cyclohexylamine, morpholine, and mixtures thereof. Suitable alkali or alkaline earth metal hydroxides include, for example, sodium hydroxide and potassium hydroxide. In some embodiments, the neutralizer is selected from one or more of 2-amino-2 methyl-1,3-propanediol, 2 amino-2-methyl-1-propanol, N,N-dimethyl-2-amino-2-methyl-1-propanol, potassium hydroxide, triethanolamine, and triisopropanolamine. Mixtures of suitable neutralizing compounds are also suitable.

Among embodiments in which neutralizing compound is used, the molar equivalent ratio of neutralizing compound to acid-functional groups on polymer (a) is, for example, 0.05 or higher, or 0.1 or higher, or 0.5 or higher, or 0.75 or higher. Independently, among embodiments in which neutralizing compound is used, the molar equivalent ratio of neutralizing compound to acid-functional groups on polymer (a) is, for example, 1.1 or lower.

Among embodiments in which one or more adjuvant is used, adjuvants may include, for example, one or more polymers other than polymer (a) (or polymer (AA)), one or more of preservatives (including, for example, one or more of organic acids, isothiazolones, iodopropynylbutyl carbamate, benzyl alcohol, imidazolidinylurea and alkyl parabens); thickeners; moisturizers (such as glycerine, hydrolyzed silk protein, and hydrolyzed wheat protein); conditioning agents such as panthenol; conditioning agents (U.S. Pat. No. 5,164,177 may be consulted for further general and specific details on suitable conditioning agents); emulsifiers; antistatic aids; extracts; proteins; vitamins; colorants; UV protectors; fragrances, and corrosion inhibitors. In some embodiments, no adjuvant is used.

In some embodiments in which one or more adjuvant is used, the ratio of the weight of the total amount of adjuvants to the weight of polymer (a) (or polymer (AA)) is 0.01:1 or higher; or 0.05:1 or higher; or 0.1:1 or higher. Independently, in some embodiments in which one or more adjuvant is used, the ratio of the weight of the total amount of adjuvants to the weight of polymer (a) (or polymer (AA)) is 1.4:1 or lower; or 1.2:1 or lower; or 1.1:1 or lower.

Among embodiments in which one or more polymer other than polymer (a) (or polymer (AA)) is used in the composition of the present invention, a polymer other than polymer (a) (or polymer (AA)) may be one or more hair fixative polymers such as, for example, butyl acrylate/ethyl acrylate/methacrylic acid copolymers, poly(vinyl pyrrolidone)/vinyl acetate copolymers, octylacrylamide/acrylates/butylaminoethyl-methacrylate copolymers, vinylcaprolactam/vinyl-pyrrolidone/dimethylaminoethyl-methacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, and polyesters. Additional hair fixative polymers that may be useful for blending with polymer (a) (or polymer (AA)) include, for example (by INCI name), PVP/VA copolymer, ethyl ester of PVM/MA copolymer, butyl ester of PVM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyester acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, PVP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, Octylacrylamide/Acrylates/Butylaminoethyl Methacrylate Copolymer, Vinyl caprolactam/VP/Dimethylaminoethyl Methacrylate Copolymer, Acrylates/t-Butylacrylamide Copolymer, Acrylates/C1-2 Succinates/Hydroxyacrylates Copolymer, Acrylamide/Sodium Acryloyldimethyltaurate/Acrylic Acid Polymer and mixtures thereof.

Among embodiments in which one or more polymer other than polymer (a) (or polymer (AA)) is used in the composition of the present invention, a polymer other than polymer (a) (or polymer (AA)) may be one or more rheology modifier polymers such as, for example, Acrylates Steareth-20 Methacrylate Copolymer, Acrylates Beheneth-25 Methacrylate Copolymer, Acrylates Steareth-20 Methacrylate Crosspolymer, Acrylates Copolymer, Acrylates/Vinylneodecanoate Crosspolymer, and mixtures thereof.

In some embodiments, every polymer in the hair styling composition is a polymer (a) (or polymer (AA)). Independently, in some embodiments, exactly one polymer (a) (or polymer (AA)) is used. In embodiments in which exactly one polymer (a) (or polymer (AA)) is used, polymer (a) (or polymer (AA)) will show the usual distributions around characteristics such as, for example, molecular weight, glass transition temperature, and particle size, but polymer (a) (or polymer (AA)) will not be a blend of two or more different polymers with distinct characteristics.

The water in the composition of the present invention may be introduced into the composition by any method. It is contemplated, for example, that water may be added directly to the composition. It is also contemplated, for example, that polymer (a) (or polymer (AA)) may be made by emulsion polymerization to produce a polymer latex, and that latex, containing both polymer (a) (or polymer (AA)) and water, may be added to the composition. Also contemplated are embodiments in which some water is added to the composition directly and some water is added as part of a polymer latex.

In some embodiments, the hair styling composition of the present invention does not contain any silicone compound. Independently, in some embodiments, the hair styling composition of the present invention does not contain any plasticizer. Independently, in some embodiments, the hair styling composition of the present invention does not contain divalent metal cations in amounts sufficient to cause crosslinking. In some embodiments, no divalent metal cations are added to the hair styling composition of the present invention. In some embodiments, no divalent metal cations are present in the hair styling composition of the present invention.

In some embodiments, the hair styling composition of the present invention is fully soluble. That is, when all ingredients except for propellant (if any is to be used) are mixed together, and the resulting solution is measured for turbidity as described in the Examples below, the turbidity result is 120 NTU or lower in a solution with 12% polymer solids or is 100 NTU or lower in a solution with 10% polymer solids.

In some embodiments, polymer (a) (or polymer (AA)) is produced by emulsion polymerization. Emulsion polymerization is a well known process, described, for example, by M. S. El-Aasser in "Emulsion Polymerization" (Chapter 1 of *An Introduction to Polymer Colloids*, edited by F. Candau and R. H. Ottewill, Kluwer Academic Publishers, 1990).

In some embodiments that employ emulsion polymerization, the process used is aqueous emulsion polymerization.

Emulsion polymerization involves the use of one or more surfactant. In some embodiments, the emulsion process for producing polymer involves the use of one or more nonionic surfactant.

Suitable nonionic surfactants include, for example, polyoxyalkylene surfactants, polyalkylene glycol esters, polyoxyethylene derivatives of fatty acid esters of polyhydric alcohols, fatty acid esters of polyalkoxylated polyhydric alcohols, polyalkoxylated natural fats and oils, polyalkylene oxide block copolymers, and mixtures thereof. Among the suitable polyoxyalkylene surfactants, some suitable examples are polyoxyethylene surfactants, including, for example, alcohol alkoxylates, alkylphenol alkoxylates, and mixtures thereof. Suitable alcohol alkoxylates include, for example, alcohol ethoxylates and alcohol propoxylates. In some embodiments, one or more alcohol ethoxylate is used. In some embodiments, one or more secondary alcohol ethoxylate is used. In some embodiments, every nonionic surfactant used in the polymerization of polymer (a) (or polymer (AA)) is a secondary alcohol ethoxylate.

In some embodiments, the amount of nonionic surfactant used in the emulsion polymerization is 0.5% to 12% by weight based on the total weight of monomers used in the polymerization. In some embodiments, the amount of nonionic surfactant, by weight based on the total weight of monomers used in the polymerization, is 1% or more; or 2% or more; or 5% or more. Independently, in some embodiments, the amount of nonionic surfactant, by weight based on the total weight of monomers used in the polymerization, is 10% or less; or 8% or less.

In some embodiments, no anionic surfactant is used in the emulsion polymerization process. In some embodiments, one or more anionic surfactant is used in the emulsion polymerization process in addition to the one or more nonionic surfactant. Suitable anionic surfactants include, for example, sulfosuccinates, sulfonates, and sulfates. Associated with each anionic surfactant is a cation; suitable cations include, for example, ammonium, cation of an alkali metal, and mixtures thereof.

Independently, in some embodiments, the emulsion polymerization process uses no cationic surfactant. Independently, in some embodiments, the emulsion polymerization process uses no zwitterionic surfactant.

In some embodiments in which one or more anionic surfactant is used, one or more alkyl polyalkoxylate sulfate surfactant is used. Alkyl polyalkoxylate sulfate has the structure

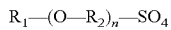

where $R_1$ and $R_2$ are alkyl groups and n is 1 to 1,000. In some embodiments, $R_1$ has 6 or more carbon atoms, or 8 or more carbon atoms. In some embodiments, $R_1$ is lauryl. In some embodiments, $R_2$ has 2 or 3 carbon atoms or a mixture thereof. In some embodiments, —$R_2$— is —$CH_2CH_2$—. In some embodiments, n is 10 or higher, or 30 or higher, or 50 or higher. Independently, in some embodiments, n is 200 or lower, or 100 or lower, or 75 or lower. In some embodiments, every anionic surfactant that is used in the polymerization of polymer (a) (or polymer (AA)) is an alkyl polyalkoxylate sulfate surfactant.

In some embodiments in which one or more anionic surfactant is used, the amount of anionic surfactant is 0.02% to 1%, by weight based on the total weight of monomers used in the polymerization. Independently, in some embodiments in which one or more anionic surfactant is used, the amount of anionic surfactant is, by weight based on the total weight of monomers used in the polymerization, 0.01% or more; or 0.03% or more. Independently, in some embodiments in which one or more anionic surfactant is used, the amount of anionic surfactant is, by weight based on the total weight of monomers used in the polymerization, 0.8% or less; or 0.4% or less; or 0.2% or less.

In some embodiments, each surfactant is fully soluble. A surfactant is considered fully soluble herein if it passes the following test. The surfactant to be tested is added to 100% ethanol (200 proof, denatured) to form a test mixture. The amount of surfactant used in the test mixture is 0.50 g actives added to 20 g of ethanol. The solution is stirred for 5 minutes and tested for turbidity as described below. A soluble surfactant is taken to be one which has less than 100 NTU haze units by this test, and shows no visible precipitate after standing for 20 minutes.

It is to be understood that in the present specification and claims, all operations and measurements, unless stated otherwise in specific cases, are conducted at 25° C.

EXAMPLES

In the following examples, the following terms and test procedures are used:

| | |
|---|---|
| BA = | butyl acrylate |
| MMA = | methyl methacrylate |
| HEMA = | hydroxyethyl methacrylate |
| MAA = | methacrylic acid |
| Sty = | styrene |
| BzA = | benzyl acrylate |
| EHA = | 2-ethylhexyl acrylate |
| n-DDM = | n-dodecyl mercaptan |
| t-DDM = | t-dodecyl mercaptan |
| 3-MBP = | 3-mercapto-butyl propionate |
| 15-S-40 = | Tergitol ™ 15-S-40 secondary alcohol ethoxylate from Dow Chemical Co. |
| FES-61 = | Disponil ™ FES-61 fatty alcohol polyglycol ether sulfate, sodium salt, from Cognis Co. |
| FES-77 = | Disponil ™ FES-77 fatty alcohol ether sulfate, sodium salt, from Cognis Co. |
| AMP-95 = | Aminomethyl propanol, from Angus Chemical Co. |
| DS-4 = | sodium dodecylbenzensulfonate, Polystep ™ A-16-22, from Stepan Co. |

| | |
|---|---|
| RS-610 = | Rhodafac ™ RS-610-A-25, ammonium phosphate ester from Rhodia, Inc. |
| ALS = | ammonium lauryl sulfate, Polystep ™ B-7, from Stepan Co. |

Molecular Weight

Samples were dissolved in THF (2 mg solid polymer per ml of THF), shaken overnight, and filtered through a 0.45 micrometer PTFE filter. Analysis was performed by size exclusion chromatography (SEC) using a liquid chromatograph including Agilent™ Model 1100 isocratic pump, autosampler, degasser (all from Waldbronn, Co., Germany) and Waters™ Model 2414 differential refractometer (Milford Co.), at 40° C. Column set contained three PLgel columns (5 micrometer, 300×7.5 mm) connected in series, with respective pore sizes of 100, 1,000, and 10,000 Angstrom units. Injection volume was 100 microliter. Data acquisition and processing were performed using Cirrus™ Software, version 3.0, from Polymer Laboratories, UK. Molar mass data were determined via ten-point standard curve acquired from preparations of two commercially available, pre-weighed polystyrene reference mixes, using third order fitting. Reported quantities are Mw (weight-average molecular weight) and Mw/Mn (quotient obtained by dividing Mw by Mn, the number-average molecular weight). The designation "Mw (k)" means Mw divided by 1,000.

Preparation of Sample Solution at 12% Polymer Solids

Sample solution was prepared as follows. A sample of a latex or solution is neutralized with AMP-95, either by calculating the amount of AMP-95 to be equivalent to the acid groups on polymer (a) or by titrating to a pH value of 7.5. An amount of neutralized latex polymer is chosen to contain 6 grams of solid polymer. That chosen amount of neutralized latex polymer is mixed with 30.0 g ethanol and sufficient water to make the total weight of the solution 50.0 g.

Preparation of Sample Solution at 10% Polymer Solids

Same as the sample preparation at 12% (as described above) except that an amount of neutralized latex polymer is chosen to contain 5 grams of solid polymer.

Viscosity

The sample solutions were tested at 25° C. using Brookfield viscometer model DV-II+ at 12 rpm. The spindle was chosen to give a reading on the viscometer between 20 and 80 percent of full scale. Results are reported in millipascal*seconds (mPa*s), which is equivalent to centipoise. Results are reported as V12 (viscosity in mPa*s of sample solution at 12% polymer solids) or V10 (viscosity in mPa*s of sample solution at 10% polymer solids).

A polymer is considered to have acceptable viscosity if V12 is 50 mPa*s or less or if V10 is 30 mPa*s or less.

Turbidity

A sample solution was placed in a vial of size 30 ml (1 ounce) and measured using HF Scientific Micro 100 Laboratory Turbidimeter, using specifications published by the United States Environmental Protection Agency as EPA method 180.1 (Nephelometric Method). Results are reported Nephelometric Turbidity Units (NTU), as T12 (turbidity in NTU of sample solution at 12% polymer solids) or T10 (turbidity in NTU of sample solution at 10% polymer solids).

A polymer is considered to have acceptable turbidity if it has T12 of 120 NTU or lower of if it has T10 of 100 NTU or lower.

A soluble surfactant is taken to be one which has less than 100 NTU haze units by this test, and shows no visible precipitate after standing for 20 minutes.

Shine:

The tests used to evaluate shine are described below in Examples 4 and 7 below. In Table 3 below, the shine results are a ranking of best (value of 1) to worst (value of 5), based on the results presented in Example 4 below.

Hold:

The "hold" property was evaluated by three different tests: Loop Deformation, Curl Retention, and High Humidity Curl Retention.

The Loop Deformation test measures the work to compress a curl of hair 25% of its initial diameter. Compression was repeated 5 times for each tress. Measurements were conducted at 21° C. (70° F.) and 46% humidity. A Dia-Stron MTT-175 (Dia-Stron Ltd) miniature tensile tester was used.

Test conditions:
 Compression=25%
 Cycles=5
 Rate=120 mm/min
 Diameter=30 mm
 Contact Force=5
 Maximum Force=2000

Hair tresses were ER dark brown hair tresses; each tress was 2.0 g±0.1 g. The length of each uncurled hair tress was 200 mm. Tresses were washed with clarifying shampoo and warm water and then air dried. Tresses were re-wet and curled onto a 65 mm×20 mm curler and held in place with a bobby pin. The curled tresses were air dried at 21° C. for 16 hours. Dry curled tresses were sprayed with an aerosol hairspray for 2 seconds on the front and back from a distance of 20.3 cm (8 inches). Curled, treated tresses were dried for a minimum of 2 h in a controlled environment at 25° C. (77° F.) and 44% humidity.

Aerosol sprays were formulated as follows (parts by weight): 50 parts dimethyl ether, 30 parts ethanol, 15 parts water, and 5 parts solid polymer and aminomethylpropanol. Just prior to testing, the curler was carefully removed from the tress without uncurling. The curled tress was placed in the miniature tensile tester and the work required for curl compression was measured. Work values are average of results for 3 tresses and are reported in units of gmf (i.e., gram force).
 W1=work required for first compression
 W5=work required for fifth compression
 % SR=Stiffness Retention=100×W5/W1

The treated hair is considered to be acceptably stiff when the work required for compression is 200 gram force or higher. Stiffness Retention values of 90% or higher are acceptable.

High Humidity Curl Retention measures the ability of treated hair to hold its shape. Tresses (like those used in the Loop Deformation test) with initial uncurled length of 200 mm were washed with clarifying shampoo and warm water and then air dried. Tresses were re-wet and curled onto a 60 mm×20 mm curler and held in place with a bobby pin. The curled tresses were air dried at 21° C. for 16 h. Dry curled tresses were treated by spraying for 2 seconds on the front and back from a distance of 20.3 cm (8 inches). Curled, treated tresses were dried for a minimum of 1 h in a controlled environment at 25° C. (77° F.) and 44% humidity.

Curls were carefully removed from curler. Initial curl length was measured. Tresses were placed into a high humidity chamber (25° C., 88% humidity) and removed at intervals for measurement of tress length.

Aerosol sprays were formulated as in the Loop Deformation test. Each reported result is the average of three tresses. Reported quantities (in mm) are
 L0=initial curl length
 L1=curl length after 1 hour
 L4=curl length after 4 hours
 L24=curl length after 24 hours Also reported is the percent curl retention at 24 hours ("% CR24"), which is calculated as follows: % CR24=100*(200−L24)/(200−L0)

Shampoo Removability

The hair tresses 20.32 cm (8 inch) long and 2.0±0.1 grams (European Brown Virgin Hair, obtained from International Hair Importers, New York) were stripped with alcohol, then washed with TRESemmé Deep Cleansing Shampoo. Hair were treated with sprays, 2 seconds for both back and front of the hair swatches. Dried under room temperature, 50% Relative Humidity for 2 hr, then washed with TRESemmé Deep Cleansing Shampoo. After drying overnight at 25° C., hair swatches were evaluated by panelist for feel and flaking vs. untreated hair. If the results showed no difference vs. untreated hair, it indicates excellent shampoo removability. If very minor flaking or coated feel is observed, it indicates good shampoo removability. For visible flaking and coated feel hair is considered poor to very poor shampoo removability.

Gloss

Gloss measurements were taken after the films were allowed to dry for 1 hours. The method for determining the gloss is described in "Annual Book of ASTM Standards," Section 15, Volume 15.04, Test Procedure ASTM D 1455 (2000). A Gardner Byk Micro-Tri-Gloss meter, catalog number 4520, was used to record 80°, 60° and 20° gloss.

Example 1

Preparation of Polymer

A polymer was prepared as follows. A monomer mixture was made containing 415 g deionized water, 9.1 g of DS-4 surfactant (23%), 245 g BA, 280 g Styrene, 63 g MMA, 112 g MAA. After heating a reaction vessel containing 300 ml deionized water and 21.4 g DS-4 (23%) to 85° C. (under nitrogen), 1% of the monomer mixture was added with a 5.6 g water rinse followed by a 5 minute hold and then addition of 0.7 g ammonium persulfate (APS) in 10 g of water. This combination was held at 85° C. for 5 minutes. Then, the remaining monomer mixture was added over a period of 120 minutes along with a cofeed of 0.7 g APS, 1.4 g $K_2CO_3$, and 60 g water. A second co-feed of 600 g deionized water was also fed over a period of 120 min. After 60 minutes of the co-feed addition, a third co-feed of 1.26 g $NH_4HCO_3$ in 30 g water, was also begun and fed over a period of 60 minutes. After all co-feeds were completed, a 15 g rinse was added and the vessel was held at 85° C. for 15 minutes and then cooled to 80° C., followed by one or more chase (i.e., addition of initiator followed by a hold period at 80° C.). The product was cooled and filtered giving rise to a 2213 g sample of polymer emulsion (32.2% Solids, PS=61 nm).

Example 1A

Preparation of Polymer

After heating a reaction vessel containing 535 ml deionized water and 10 g RS-610 (25% active) to 85° C. (under nitrogen), 4.7% (65 g) of a mixture of 366 g deionized water, 10 g of RS-610-A25 surfactant (25%), 350 g BA, 400 g Styrene, 90 g MMA, 160 g MAA, and 6.0 g n-DDM was added with a 5.0 g water rinse followed by a 5 minute hold and then addition of 1.5 g ammonium persulfate (APS) in 15 g of water. This combination was held at 85° C. for 5 minutes. Then, the remaining monomer mixture was added over a period of 120 minutes. A second co-feed of 1.5 g APS and 120 g deionized water was also fed over a period of 130 min. After all co-feeds were completed, a 40 g rinse was added and the vessel was held at 85° C. for 25 minutes. The reaction mixture was chased and then cooled and filtered giving rise to a 2208 g sample of polymer emulsion (45.1% Solids, PS=158 nm).

Example 1B

Preparation of Polymer by Solution Polymerization

A polymer was prepared through a solution polymerization process as follows. A monomer mixture was made containing 700 g of reagent grade ethanol, 400 g of Styrene, 150 g of BA. 50 g of MMA, 220 g of HEMA, and 180 g of MAA. Separately, an initiator solution was prepared containing 6.7 g of Triganox 125-C75 and 123 g of reagent grade ethanol. After heating a reaction vessel containing 475 g of reagent grade ethanol, 10% of the above monomer mixture and 10% of the above initiator solution to 79° C. under nitrogen atmosphere, the remaining monomer mixture and initiator solution was added over a period of 180 minutes. After all feeds were completed, the reaction mixture was kept at 79° C. for 30 minutes. Then a second initiator solution, containing 20 g of Triganox 125-C75 and 80 g of ethanol, was fed at 79° C. for a period of 180 minutes. The product was cooled and filtered giving rise to a 2515 g sample of solution polymer (40% Solids).

Example 1C

Preparation of Polymer

A polymer was prepared through an emulsion polymerization process as follows. A monomer mixture was made containing 549 g deionized water, 18 g of RS-610 (23%), 7.5 g of Disponil FES 993, 288 g BA, 342 g Styrene, 135 g HEMA, 130.5 g MAA and 3.6 g of n-DDM. After heating a reaction vessel containing 340 ml deionized water and 7.2 g RS-610 to 85° C. (under nitrogen), 4% of the monomer mixture and 4.5 g of MAA were added with a 5 g water rinse followed by a 5 minute hold and then addition of 0.9 g ammonium persulfate (APS) in 18 g of water. This combination was held at 85° C. for 5 minutes. Then, the remaining monomer mixture was added over a period of 180 minutes along with a cofeed of 0.9 g APS and 117 g water. After all co-feeds were completed, a 45 g rinse was added and the vessel was held at 85° C. for 15 minutes and then cooled to 80° C., followed by one or more chase (i.e., addition of initiator followed by a hold period at 80° C.). The product was cooled and filtered giving rise to a 2324 g sample of polymer emulsion (40% Solids, PS=213 nm).

Example 2

Comparative Polymer Sample CPA

Using the polymerization method of Example 1, comparative polymer sample CPA was made with composition 25 BA/47 MMA/10 HEMA/18 MAA/0.6 n-DDM. The numbers are parts by weight.

Example 3

Various polymers and Test Results

Various polymers were made using the methods of Example 1 and Example 1A, and they are listed in Tables 1, 2, and 3 below. The method of Example 1 was used for Comparative Samples C1-C4. Where a surfactant or mixture of surfactants is shown, it replaced the DS-4 described in Example 1. The method of Example 1A was used for Comparative Samples C5-C8, Samples 9-10, Comparative Samples C11-C12, and Samples 13-18. Where a surfactant or mixture of surfactants is shown, it replaced the RS-610 described in Example 1A. Where a chain transfer is shown, it was added to the monomer mixture prior to addition of monomer mixture to the reaction vessel. The amounts listed for the monomers are parts by weight. The amounts listed for chain transfer agents and for surfactants are weight percent based on the total weight of monomer. Samples with sample number starting with "C" are comparatives. The abbreviation "surf1" means one surfactant, and "surf2" means another surfactant. Where an ingredient shows "—", that ingredient was not used in that sample. Where a test procedure shows "—", that test was not performed on that sample.

TABLE 1

| | Sample Number | | | | | | |
|---|---|---|---|---|---|---|---|
| | C1 | C1A | C2 | C3 | C4 | C5 | C6 |
| Sty | 40 | 40 | 40 | 40 | 40 | 40 | 40 |
| BA | 35 | 35 | 35 | 35 | 35 | 35 | 35 |
| MMA | 9 | 9 | 9 | 9 | 9 | 9 | 9 |
| MAA | 16 | 16 | 16 | 16 | 16 | 16 | 16 |
| HEMA | 0 | 0 | 0 | 0 | 0 | 0 | 0 |
| BzA | 0 | 0 | 0 | 0 | 0 | 0 | 0 |
| CTA | — | n-DDM | n-DDM | n-DDM | 3-MBP | n-DDM | n-DDM |
| CTA % | 0 | 0.2 | 0.4 | 0.6 | 0.48 | 0.6 | 0.6 |
| Surf1 | DS-4 | DS-4 | DS-4 | DS-4 | DS-4 | RS-610 | ALS |
| Surf1 % | 1.0 | 1.0 | 1.0 | 1.0 | 1.0 | 0.5 | 0.5 |
| Mw (k) | 366 | 172 | 95 | 67 | 66 | 62 | 65 |
| Mw/Mn | 5.3 | 3.4 | 2.7 | 2.4 | 2.4 | 2.8 | 2.5 |
| T12 | 45 | 142 | 84 | 947 | 825 | 270 | 236 |
| T10 | — | — | — | — | — | — | — |
| cP 12% | 742 | 133 | 83 | 44 | 37 | 33 | 35 |

Scrutiny of Samples C1, C1A, C2, C3, C4, and C5 shows that increasing chain transfer agent decreased the viscosity and also increased the turbidity. Among these samples, all of which had only anionic surfactant, there was no sample that had both acceptable viscosity and acceptable turbidity.

Scrutiny of Samples C3, C5, and C6 shows that turbidity remained unacceptable over a wide range of anionic surfactants.

TABLE 2

| | Sample Number | | | |
|---|---|---|---|---|
| | C7 | C8 | 9 | 10 |
| Sty | 40 | 40 | 40 | 40 |
| BA | 25 | 25 | 25 | 25 |
| MMA | 9 | 9 | 9 | 9 |
| MAA | 16 | 16 | 16 | 16 |
| HEMA | 10 | 10 | 10 | 10 |
| BzA | 0 | 0 | 0 | 0 |
| CTA | n-DDM | n-DDM | n-DDM | n-DDM |
| CTA % | 0.6 | 0.8 | 0.8 | 0.8 |
| Surf1 | RS-610 | RS-610 | 15-S-40 | 15-S-40 |
| Surf1 % | 0.5 | 0.5 | 6 | 6 |
| Surf2 | — | — | — | FES-77 |
| Surf2 % | — | — | — | 0.1 |
| Mw (k) | — | 49 | 80 | 88 |
| Mw/Mn | — | 2.5 | 5.3 | 4.9 |
| T12 | 157 | 290 | 5.4 | — |
| T10 | — | — | — | 53 |
| cP 12% | 33 | 27 | 37 | — |
| cP 10% | — | — | — | 24 |

Scrutiny of Samples C5 and C7 shows that, among samples that both have anionic surfactant and both have unacceptable turbidity, the turbidity was improved in the sample with HEMA in the polymer.

Scrutiny of samples C8, 9, and 10 shows that when anionic surfactant is used, turbidity was improved without making the viscosity unacceptable.

TABLE 3

| | Sample Number | | | | | | | |
|---|---|---|---|---|---|---|---|---|
| | C11 | C12 | 13 | 14 | 15 | 16 | 17 | 18 |
| Sty | 0 | 20 | 30 | 40 | 50 | 40 | 40 | 40 |
| BA | 65 | 45 | 35 | 25 | 15 | 25 | 23 | 25 |
| MMA | 9 | 9 | 9 | 9 | 9 | 9 | 9 | 9 |
| MAA | 16 | 16 | 16 | 16 | 16 | 16 | 18 | 16 |
| HEMA | 10 | 10 | 10 | 10 | 10 | 10 | 10 | 0 |
| BzA | 0 | 0 | 0 | 0 | 0 | 0 | 0 | 34 |
| CTA | n-DDM | n-DDM | n-DDM | n-DDM | n-DDM | t-DDM | t-DDM | t-DDM |
| CTA % | 0.8 | 0.8 | 0.8 | 0.8 | 0.6 | 0.6 | 0.6 | 0.6 |
| Surf1 | 15-S-40 | 15-S-40 | 15-S-40 | 15-S-40 | 15-S-40 | 15-S-40 | 15-S-40 | 15-S-40 |
| Surf1 % | 6 | 6 | 6 | 6 | 6 | 6 | 6 | 6 |
| Surf2 | FES-61 | FES-61 | FES-61 | FES-61 | FES-61 | FES-61 | FES-61 | FES-61 |
| Surf2 % | 0.1 | 0.1 | 0.1 | 0.1 | 0.1 | 0.1 | 0.1 | 0.1 |
| Mw (k) | 88 | 54 | 59 | 59 | 81 | 53 | 50 | 50 |
| Mw/Mn | 4.9 | 3.6 | 3.9 | 3.9 | 5.1 | 2.8 | 2.8 | 2.8 |
| T12 | — | — | — | — | — | — | — | — |
| T10 | 0.8 | 17 | 29 | 89 | 4.4 | 5.5 | 3.5 | 18 |
| cP 12% | — | — | — | — | — | — | — | — |
| cP 10% | 17 | 17 | 21 | 22 | 27 | 20 | 21 | 24 |
| Shine rank | 4 | 5 | 3 | 2 | 1 | — | — | — |

Scrutiny of Samples C11, C12, 13, 14, and 15 shows that, among samples that had acceptable turbidity and acceptable viscosity, the samples with the highest levels of styrene had the best shine.

Scrutiny of Samples 14, 16, 17, and 18 shows that, acceptable turbidity and acceptable viscosity resulted from levels of t-DDM that were lower than the level of n-DDM used in Sample 14. The benefit of the use of t-DDM is shown for a variety of polymer compositions.

Example 4

Hair Styling Compositions

Aerosol concentrate compositions were made using some of the Sample Polymers listed in Example 3. Polymer latex was added in sufficient amount to give the polymer solids shown below. AMP-95 was added in amount sufficient to neutralize 100% of the acid content of the polymer. Each formulation was as follows:

| ethanol | 80.0 g |
|---|---|
| AMP-95 | 0.47 g |
| solid polymer | 4 or 5 g |
| water | to make 100 g total |

The formulations were as follows:

| Formulation | Polymer | amount of solid polymer (g) |
|---|---|---|
| CA (comparative) | CPA | 5 |
| CB (comparative) | C11 | 5 |
| CC (comparative) | C12 | 5 |

-continued

| Formulation | Polymer | amount of solid polymer (g) |
|---|---|---|
| D | 13 | 5 |
| E | 14 | 5 |
| F | 15 | 5 |
| G | 15 | 4 |

Example 4

Testing 1.5 g of each formulation was pipetted onto a matte black panel, allowed to dry, and then inspected by nine trained observers. Each observer assigned a rating to each panel of from 1 (matte) to 5 (shiny). The results were as follows:

| Observer | CA | CB | CC | D | E | F | G |
|---|---|---|---|---|---|---|---|
| J1 | 2 | 2 | 3 | 3 | 4.5 | 5 | 3 |
| S | 2 | 2 | 3 | 4 | 5 | 5 | 1 |
| M1 | 3 | 3 | 3 | 2 | 5 | 5 | 2 |
| C1 | 4 | 3 | 2 | 3 | 5 | 5 | 2 |
| K | 3 | 4 | 2 | 3.5 | 3 | 2 | 3 |
| J2 | 1 | 0 | 2 | 2 | 3 | 5 | 4 |
| C2 | 1 | 3 | 2 | 3 | 4 | 5 | 2 |
| M2 | 3 | 3 | 3 | 3 | 4 | 5 | 2 |
| D | 2 | 3 | 2 | 2 | 4 | 5 | 2 |

The inventive compositions had generally better shine than the comparative compositions. The scores in each column can be added together to yield a total score for each formulation. According to those totals, the most shiny sample (i.e., the one with the highest total score) was formulation F, followed by (in order of decreasing total score) E, then D, then CB, then CC, then a tie between CA and G.

Example 5

Additional Polymer

Using the method of Example 1, Polymer PH was made, without n-DDM, with monomer composition 40 Sty/35 BA/9 MMA/16 MAA. Polymer PH was used to make formulation H by the method of Example 4, with 4% polymer solids. Mw was 383,000.

Example 6

Additional Comparatives

Using the method of Example 5, a comparative aerosol hair spray composition (CPJ) was made at 4% polymer solids, using polymer Amphomer™ LV-71 (octylacrylamide/acrylates/butylaminoethyl methacrylate copolymer, from National Starch Co.). Comparative composition CPK was a commercial shine spray, and comparative composition CPL was a commercial high-VOC aerosol spray that contains Amphomer™ 28-4910 (octylacrylamide/acrylates/butylaminoethyl methacrylate copolymer, from National Starch Co.).

Example 7

Additional Testing

Bleached blonde hair tresses (2.0 g each) were sprayed with compositions from 15 cm (6 inches) distance, allowed to dry, and weighted. Procedure was repeated until each tress had a total of 0.01 g of dried composition. Ten trained panelists inspected the hair and rated each tress from 1 (matte) to 5 (shiny). The average of the ten ratings is shown for each composition. Results were as follows:

| Composition | Average Rating |
|---|---|
| untreated | 1.2 |
| PH | 4.3 |
| CPK | 4.5 |
| CPL | 2.5 |
| CPJ | 1.8 |

Example 8

Results of Loop Deformation Tests

Delivery rate for each spray:
  Acudyne 180: 0.58 g/sec
  Sample 14: 0.52 g/sec
  Sample 15: 0.61 g/sec
Results:

| Polymer | W1 (gmf) | W5 (gmf) | % SR |
|---|---|---|---|
| Untreated | 20.8 | 19.7 | 94.7% |
| Acudyne ™ 180 | 96.8 | 92.1 | 95.1% |
| Sample 14 | 259.3 | 236.1 | 91.1% |
| Sample 15 | 251.1 | 232.4 | 92.6% |

Results indicate good stiffness from Samples 14 and 15 compared to Acudyne™ 180 and untreated hair tress control. Samples 14 and 15 also have good stiffness retention. Acudyne™ 180 has no monomer (i).

Example 9

Results of High Humidity Curl Retention Tests

Delivery rate for each spray:
  Acudyne™ 180: 0.58 g/sec
  Sample 14: 0.52 g/sec
  Sample 15: 0.61 g/sec
Results (each result is average of 3 tresses)

| Polymer | L0 (mm) | L1 (mm) | L4 (mm) | L24 (mm) | % CR24 |
|---|---|---|---|---|---|
| Untreated | 87 | 185 | 192 | 192 | 7% |
| Acudyne ™ 180 | 44 | 92 | 114 | 140 | 38% |
| Sample 14 | 35 | 45 | 49 | 54 | 88% |
| Sample 15 | 26 | 70 | 92 | 108 | 53% |

Results indicate good retention of hold under high humidity conditions for test samples.

Example 10

Solubility of Surfactants

Surfactants were tested for solubility. 0.5 g of active surfactant was added to 100% ethanol (200 proof, denatured)

and stirred for 5 minutes. Turbidity was measured as described above. Results were as follows:

| Surfactant Name | Turbidity (NTU) | Appearance of Ethanol Solution |
|---|---|---|
| Tergitol 15-S-40 | 0.27 | Crystal Clear |
| FES-61 | 69 | Trace of Haze |
| FES-77 | 69 | Trace of Haze |
| Sodium dodecylbenzene-sulfonate (DS-4) | 136 | Hazy suspension and precipitate which slowly settles out |
| Ammonium Lauryl Sulfate (Polystep B7) | 450 | High haze suspension and precipitate which slowly settles out |
| Rhodafac RS-610-A-25 | 495 | High haze suspension and precipitate which slowly settles out |
| Water Control | 0.12 | Crystal Clear |

Example 11

Additional Shine Data

Hair styling compositions were prepared as follows. The following ingredients were mixed:

dimethyl ether, 50 g polymer in latex form, to give 5 g of solid polymer (approximately 12.3 g of latex)

AMP-95, to neutralize 100% of the acid groups (approximately 0.9 g)

SD Alcohol 40B, from Pharmaco, to give total of 100 g (approximately 37 g)

The mixing was performed as follows: SD Alcohol 40B was charged to the mixing vessel. Polymer in latex form was added with stirring. AMP-95 was added with stirring (mixture became clear) Dimethyl ether was charged under pressure.

To evaluate shine, 2.0 g hair tresses were treated with aerosol spray from a distance of 8 inches. Treatment level was 0.02 g dried formulation on tress. Tresses were either bleached blonde or European dark brown virgin hair. The tresses were evaluated in a shine box by six panelists. Results of the six panelists were averaged to give the rating. The rating scale was from 0 (flat, matte), in half-unit steps to 5 (high shine, gloss).

Average Ratings were as follows:

| Sample | Bleached Blonde Hair | Brown Hair |
|---|---|---|
| untreated control | 1.1 | 4.8 |
| Acudyne ™ 180 | 3 | 2.5 |
| Sample 14 | 4.4 | 2.7 |
| Sample 15 | 3.5 | 4.3 |

Example 12

Additional Polymers

Additional Polymers were made. Polymer #19 was made using Example 1B. Polymers #20-25 were made using Example 1C. The polymers were as follows:

| | Sample Number | | | | | | |
|---|---|---|---|---|---|---|---|
| | 19 | 20 | 21 | 22 | 23 | 24 | 25 |
| Sty | 40 | 38 | 32 | 35 | 35 | 35 | 35 |
| BA | 15 | 32 | 32 | 34 | 33 | 32 | 28 |
| MMA | 5 | — | — | — | — | 5 | 5 |
| MAA | 18 | 15 | 18 | 21 | 22 | 23 | 26 |
| HEMA | 22 | 15 | 18 | 10 | 10 | — | — |
| EHA | — | — | — | — | — | 5 | 6 |

Example 13

Testing

Examples 15 and 19-25 were tested. Hair styling compositions were made as in Example 11. (for Sample 19, the solution was used in place of a latex). "Clarity" is an assessment of the visual appearance, characterized as clear, slight ("sl") haze, or very slight ("v.sl.") haze. The results were as follows:

| | Sample Number | | | | | | | |
|---|---|---|---|---|---|---|---|---|
| | 15 | 19 | 20 | 21 | 22 | 23 | 24 | 25 |
| T10 | 6 | 6 | 6 | 6 | 6 | 6 | 6 | 6 |
| Clarity | clear | clear | clear | clear | sl. haze | v. sl. haze | clear | sl. haze |
| Shampoo Removability | poor | — | very poor | poor | good | good | excellent | excellent |
| Shine rating | 5 | — | 5 | 5 | 5 | 5 | 5 | 5 |
| Hold (W1-gmf) | 165 | — | 90 | — | 128 | 107 | 90 | — |
| Hold (W5-gmf) | 159 | — | 84 | — | 118 | 99 | 86 | — |
| Hold (% SR) | 96 | — | 93 | — | 92 | 92 | 96 | — |
| CR24 (%) | 82 | — | 70 | — | 78 | 75 | 78 | — |
| Gloss (20°) | 38 | — | 68 | — | 60 | 59 | 75 | — |
| Gloss (60°) | 82 | — | 92 | — | 91 | 89 | 92 | — |
| Gloss (80°) | 101 | — | 118 | — | 96 | 95 | 110 | — |

Example 14

Hair Styling Gel

The following is an example of a hair styling gel that uses Sample 24 of Example 12 above. It is expected that this hair styling gel will have desirable properties.

| Ph | Trade Name | % Wt. | CTFA/INCI Name | Supplier |
|---|---|---|---|---|
| A | Water | q.s. to 100 | Water | |
| A | Polymer sample 24 in Example #12 | 4.44 | | Rohm and Haas |
| A | Versene | 0.01 | Tetrasodium EDTA | Dow Chemical |
| A | AMP-95 | 0.89 | Aminomethyl Propanol | Dow Chemical |
| B | Volpo 20 | 0.43 | Oleth-20 | Croda |
| B | Fragrance | 0.07 | | |
| B | Neolone ™ PE Preservative | 0.60 | Methylisothiazolinone, Phenoxyethanol | Rohm and Haas |
| B | Tagat CH40 | 0.10 | PEG-40 hydrogenated castor oil | Degussa |

-continued

| Ph | Trade Name | % Wt. | CTFA/INCI Name | Supplier |
|---|---|---|---|---|
| B | Glycerin USP | 0.30 | Glycerin | RITA |
| B | Propylene Glycol USP | 0.50 | Propylene Glycol | Fisher |
| B | Dow Corning DC-193 Surfactant | 0.20 | PEG-12 Dimethicone | Dow Corning |
| C | Silsoft ® 440 | 0.20 | PEG/PPG-20/23 Dimethicone | GE Silicones |
| C | Aculyn ™ 88 Rheology Modifier | 4.14 | Acrylates/Steareth-20 Methacrylate Crosspolymer | Rohm and Haas |

Example 15

Hair Spray Composition

The following is an example of a hair spray composition that uses Sample 24 of Example 12 above. It is expected that this composition will have desirable properties.

| Ph | Trade Name Material | INCI Name | Aerosol Spray (% Wt) | Non-Aerosol Spray (% Wt) |
|---|---|---|---|---|
| A | Alcohol | 96% v/vEtOH | 25.00 | 55.00 |
| A | Water | | q.s. to 100 | q.s. to 100 |
| A | Polymer sample 24 in Example #12 | | 12.50 | 12.50 |
| A | AMP-95 | Aminomethyl Propanol | 1.33 | 1.33 |
| A | Mirasil HMS | Disiloxane | 0.20 | 0.20 |
| B | DME | d = 0.66 | 30.00 | 0.00 |

We claim:

1. A hair styling composition comprising
   (a) one or more fully soluble polymer comprising, as polymerized units,
      (i) 30% to 75% by weight, based on the weight of said polymer, one or more monomer that has refractive index of 1.490 or higher,
      (ii) 1% to 30% by weight, based on the weight of said polymer, one or more acid-functional monomer, and
      (iii) 5% to 69% by weight, based on the weight of said polymer, one or more additional monomer,
   (b) solvent-propellant mixture comprising
      (i) 0% to 75% by weight, based on the weight of said solvent-propellant mixture, propellant,
      (ii) 5% to 95% by weight, based on the weight of said solvent-propellant mixture, volatile organic solvent, and
      (iii) 0% to 50% by weight, based on the weight of said solvent-propellant mixture, water,
   (c) neutralizer, wherein the mole ratio of said neutralizer to the acid-functional groups on said polymer (a) is from 0:1 to 1.1:1, and
   (d) one or more adjuvants, wherein the ratio of the total weight of all adjuvants to the weight of said polymer (a) is from 0:1 to 1.4:1,
   wherein the amount of said polymer (a) is 1% to 10% by weight based on the sum of the weights of said polymer (a) and said solvent-propellant mixture (b),
   wherein the amount of said solvent-propellant mixture (b) is 90% to 99% by weight based on the sum of the weights of said polymer (a) and said solvent-propellant mixture (b).

2. The composition of claim 1, wherein said monomer (i) comprises one or more vinyl aromatic monomer.

3. The composition of claim 1, wherein said monomer (iii) comprises one or more hydroxyalkyl (meth)acrylate.

4. The composition of claim 1, wherein said monomer (iii) comprises 0% to 5% hydroxyalkyl (meth)acrylate, and wherein the amount of said monomer (ii) is 20% or more, by weight based on the weight of said polymer.

5. A hair styling composition comprising
   (AA) one or more fully soluble polymer comprising, as polymerized units,
      (i) 30% to 75% by weight, based on the weight of said polymer, one or more monomer that has refractive index of 1.490 or higher,
      (ii) 1% to 30% by weight, based on the weight of said polymer, one or more acid-functional monomer, and
      (iii) 5% to 69% by weight, based on the weight of said polymer, one or more additional monomer,
   (BB) solvent mixture comprising
      (i) 0% to 50% by weight, based on the weight of said solvent mixture, volatile organic solvent, and
      (ii) 50% to 100% by weight, based on the weight of said solvent mixture, water,
   (c) neutralizer, wherein the mole ratio of said neutralizer to the acid-functional groups on said polymer (AA) is from 0:1 to 1.1:1, and
   (d) one or more adjuvants, wherein the ratio of the total weight of all adjuvants to the weight of said polymer (AA) is from 0:1 to 1.4:1,
   wherein the amount of said polymer (AA) is 1% to 30% by weight based on the sum of the weights of said polymer (AA) and said solvent mixture (BB), wherein the amount of said solvent mixture (BB) is 80% to 99% by weight based on the sum of the weights of said polymer (AA) and said solvent mixture (BB).

6. The composition of claim 1, wherein said polymer (a) has Mw of 25,000 to 300,000.

7. The composition of claim 1, wherein said composition comprises one or more surfactant, and wherein each said surfactant in said composition is fully soluble.

8. The composition of claim 1, wherein said solvent-propellant mixture comprises
   (i) 0% by weight, based on the weight of said solvent-propellant mixture, propellant,
   (ii) 75% to 95% by weight, based on the weight of said solvent-propellant mixture, volatile organic solvent having boiling point of 30° C. or higher, and
   (iii) 5% to 25% by weight, based on the weight of said solvent-propellant mixture, water.

9. The composition of claim 1, wherein said solvent-propellant mixture comprises
   (i) 0% by weight, based on the weight of said solvent-propellant mixture, propellant,
   (ii) 99% to 100% by weight, based on the weight of said solvent-propellant mixture, volatile organic solvent having boiling point of 30° C. or higher, and (iii) 0% to 1% by weight, based on the weight of said solvent-propellant mixture, water.

10. The composition of claim 1 wherein said polymer (a) does not include any polymerized unit of any monomer that is a vinyl lactam.

11. The composition of claim 10, wherein said monomer (i) comprises one or more vinyl aromatic monomer.

12. The composition of claim 10, wherein said monomer (iii) comprises one or more hydroxyalkyl (meth)acrylate.

13. The composition of claim 10, wherein said monomer (iii) comprises 0% to 5% hydroxyalkyl (meth)acrylate, and wherein the amount of said monomer (ii) is 20% or more, by weight based on the weight of said polymer.

14. The composition of claim 5, wherein said polymer (AA) does not include any polymerized unit of any monomer that is a vinyl lactam.

* * * * *